US012288661B2

(12) United States Patent
He et al.

(10) Patent No.: US 12,288,661 B2
(45) Date of Patent: Apr. 29, 2025

(54) RADIOTHERAPY TARGET DEVICE

(71) Applicant: SHANGHAI UNITED IMAGING HEALTHCARE CO., LTD., Shanghai (CN)

(72) Inventors: Shoubo He, Shanghai (CN); Wei Han, Shanghai (CN); Yanfang Liu, Shanghai (CN); Chaoting Wen, Shanghai (CN); Shouzeng Dong, Shanghai (CN); Li Wang, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 245 days.

(21) Appl. No.: 17/816,996

(22) Filed: Aug. 2, 2022

(65) Prior Publication Data
US 2023/0029986 A1 Feb. 2, 2023

(30) Foreign Application Priority Data

Aug. 2, 2021 (CN) .......................... 202110882687.6
Aug. 2, 2021 (CN) .......................... 202110882692.7

(51) Int. Cl.
| | |
|---|---|
| *H01J 35/08* | (2006.01) |
| *A61N 5/10* | (2006.01) |
| *H01J 35/12* | (2006.01) |
| *H01J 35/16* | (2006.01) |
| *H01J 35/18* | (2006.01) |
| *A61N 5/00* | (2006.01) |
| *H05H 6/00* | (2006.01) |

(52) U.S. Cl.
CPC ............. *H01J 35/116* (2019.05); *H01J 35/13* (2019.05); *H01J 35/16* (2013.01); *H01J 35/18* (2013.01); *A61N 2005/005* (2013.01); *A61N 2005/1092* (2013.01); *H01J 2235/1204* (2013.01); *H01J 2235/1262* (2013.01); *H01J 2235/166* (2013.01); *H01J 2235/18* (2013.01); *H05H 6/00* (2013.01); *H05H 2277/11* (2013.01)

(58) Field of Classification Search
None
See application file for complete search history.

(56) References Cited

U.S. PATENT DOCUMENTS

| | | | |
|---|---|---|---|
| 5,010,562 A * | 4/1991 | Hernandez | ............... H05H 7/00 378/126 |
| 5,471,516 A * | 11/1995 | Nunan | ................. A61N 5/1049 378/65 |
| 6,721,392 B1 | 4/2004 | Dinsmore | |

(Continued)

FOREIGN PATENT DOCUMENTS

| | | |
|---|---|---|
| CN | 105263251 A | 1/2016 |
| CN | 108366483 A | 8/2018 |

(Continued)

*Primary Examiner* — Thomas R Artman
(74) *Attorney, Agent, or Firm* — METIS IP LLC

(57) ABSTRACT

One or more embodiments of the present disclosure relate to a radiotherapy target device. The radiotherapy target device may include: a target component including a target body and a support supporting the target body; and a housing surrounding the target component. The housing may include a first surface and a second surface allowing radiation beams to pass through.

20 Claims, 19 Drawing Sheets

(56) References Cited

U.S. PATENT DOCUMENTS

| | | | | |
|---|---|---|---|---|
| 7,397,044 B2* | 7/2008 | Calderon | ............ | A61N 5/1048 |
| | | | | 250/492.1 |
| 7,831,021 B1* | 11/2010 | Schumacher | ............ | H05G 2/00 |
| | | | | 378/143 |
| 8,098,796 B2* | 1/2012 | Schumacher | ............ | H05G 2/00 |
| | | | | 378/143 |
| 8,111,806 B2* | 2/2012 | Amelia | ................ | A61N 5/1049 |
| | | | | 378/143 |
| 9,734,979 B2* | 8/2017 | Tang | ........................ | H01J 35/13 |
| 10,734,187 B2* | 8/2020 | Maltz | ..................... | H01J 35/116 |
| 11,224,766 B2* | 1/2022 | Liu | ....................... | A61N 5/1077 |
| 11,361,931 B2* | 6/2022 | Maltz | ..................... | H01J 35/116 |
| 2007/0018117 A1* | 1/2007 | Calderon | ............ | A61N 5/1048 |
| | | | | 250/492.1 |
| 2011/0051899 A1* | 3/2011 | Schumacher | ............ | H05G 2/00 |
| | | | | 156/60 |
| 2015/0078510 A1 | 3/2015 | Tang et al. | | |
| 2019/0148102 A1* | 5/2019 | Maltz | ..................... | H01J 35/116 |
| | | | | 378/130 |
| 2019/0358470 A1 | 11/2019 | Liu et al. | | |
| 2020/0357599 A1* | 11/2020 | Maltz | ..................... | H01J 35/116 |
| 2023/0029986 A1* | 2/2023 | He | ......................... | H01J 35/18 |

FOREIGN PATENT DOCUMENTS

| | | |
|---|---|---|
| CN | 108578913 A | 9/2018 |
| CN | 215916244 U | 3/2022 |
| CN | 215916245 U | 3/2022 |

* cited by examiner

RADIOTHERAPY TARGET DEVICE

CROSS-REFERENCE TO RELATED APPLICATIONS

This application claims priority of Chinese Patent Application No. 202110882692.7 filed on Aug. 2, 2021 and Chinese Patent Application No. 202110882687.6 filed on Aug. 2, 2021, the entire contents of which are hereby incorporated by reference.

TECHNICAL FIELD

The present disclosure generally relates to the field of imaging device technology, and in particular, to a radiotherapy target device.

BACKGROUND

In a radiotherapy device, high-intensity electron beams generated by an electron accelerating tube hit a target body and photons may be generated. In the process, a large amount of heat may be deposited on the target body, resulting in rapid and severe temperature changes on the surface of the target body, which may cause substances of the target body to oxidize, sublime, and deposit on an output window of the accelerating tube, resulting in damage of the output window and affecting usability. In addition, the process of replacing the output window is very complicated and expensive, increasing the cost. Therefore, it is desirable to provide an improved radiotherapy target device to ensure the performance while reducing the cost.

SUMMARY

According to an aspect of the present disclosure, a radiotherapy target is provided. The device may include a target component including a target body and a support supporting the target body; and a housing surrounding the target component. The housing may include a first surface and a second surface allowing radiation beams to pass through.

In some embodiments, the housing forms a sealed cavity.

In some embodiments, the support may include a target substrate including a through hole along a beam direction of the radiation beams; and a target seat mounted in the through hole and used to mount the target body.

In some embodiments, the target seat may include a mounting groove with an opening facing the first surface, wherein the mounting groove is used to mount the target body; and a concave part with an opening facing the second surface, wherein the concave part is used to allow the radiation beams to pass through.

In some embodiments, the target seat may include a fixed edge. The through hole may include a fixed groove. The fixed groove may be used to mount the fixed edge to mount the target seat in the through hole.

In some embodiments, an accommodating space may be formed between an outer wall of the target seat and the through hole. The accommodating space may allow a cooling component or a cooling medium to pass through.

In some embodiments, the through hole may include a first stepped hole and a second stepped hole coaxially arranged. An outer wall of the target seat may be in contact with an inner wall of the second stepped hole. The outer wall of the target seat and an inner wall of the first stepped hole may be enclosed as the accommodating space.

In some embodiments, the accommodating space may be formed by a first slot in an inner wall of the through hole and/or a second slot in an outer wall of the target seat.

In some embodiments, the support further may include a flow channel. A first end of the flow channel may be connected with a cavity formed by the support. A second end of the flow channel may be connected with outside of the support.

In some embodiments, the flow channel may be arranged on a target substrate of the support.

In some embodiments, the support may further include a first cover plate and/or a second cover plate, and the flow channel may be arranged on the first cover plate and/or the second cover plate.

In some embodiments, the second end of the flow channel may be connected with an inert-gas source or a vacuum component.

In some embodiments, the target component may further include an adsorption component arranged in the flow channel or an inner surface of the housing.

In some embodiments, the housing may further include a first window and a second window respectively arranged on the first surface and the second surface, and the first window and the second window may be located on both sides of the target body and at least partially correspond to each other, the first window and the second window allowing the radiation beams to pass through.

In some embodiments, a cross-sectional area of the second window may be larger than a cross-sectional area of the first window.

In some embodiments, a thickness of the first window or a thickness of the second window may be less than 100 microns.

In some embodiments, the housing may include a through hole connected with an inert-gas source or a vacuum component.

In some embodiments, the radiotherapy target device may further include a cooling component used to cool the target component. The cooling component may pass through the housing and may be partially located inside the housing.

In some embodiments, the radiotherapy target device may further include a second target component. The second target component includes a second target body. The target substrate further includes a second through hole along the beam direction of the radiation beams. The support further includes a second target seat mounted in the second through hole and used to mount the second target body.

According to another aspect of the present disclosure, a radiotherapy target device is provided. The radiotherapy target device may include a target component including a target body and a support supporting the target body. The support may include a flow channel. A first end of the flow channel may be connected with a cavity formed by the support. A second end of the flow channel may be connected with outside of the support.

BRIEF DESCRIPTION OF THE DRAWINGS

The present disclosure is further illustrated in terms of exemplary embodiments. These exemplary embodiments are described in detail with reference to the drawings. These embodiments are non-limiting exemplary embodiments, in which like reference numerals represent similar structures, and wherein.

DETAILED DESCRIPTION

Figure 1:
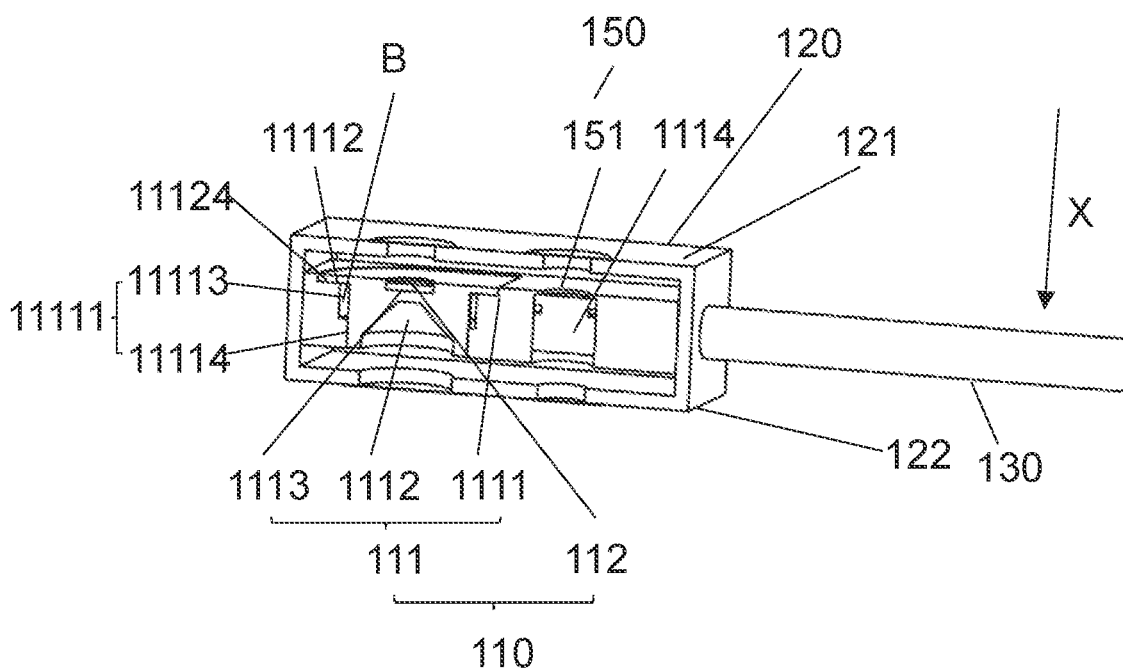
FIG. 1 is a schematic diagram illustrating a cross-sectional structure of an exemplary radiotherapy target device according to some embodiments of the present disclosure.

In order to more clearly illustrate the technical solutions related to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

It should be understood that the "system," "device," "unit," and/or "module" used herein are one method to distinguish different components, elements, parts, sections, or assemblies of different levels. However, if other words can achieve the same purpose, the words can be replaced by other expressions.

As used in the disclosure and the appended claims, the singular forms "a," "an," and "the" include plural referents unless the content clearly dictates otherwise; the plural forms may be intended to include singular forms as well. In general, the terms "comprise," "comprises," and/or "comprising," "include," "includes," and/or "including," merely prompt to include steps and elements that have been clearly identified, and these steps and elements do not constitute an exclusive listing. The methods or devices may also include other steps or elements.

An aspect of the present disclosure relates to a radiotherapy target device. The radiotherapy target device may be applied to a radiotherapy device to perform a treatment operation and/or an imaging operation on a patient. In some embodiments, the radiotherapy target device may be used in conjunction with an electron generating device. Radiation beams generated by the electron generating device may pass through the radiotherapy target device and may be converted into photons and projected onto a nidus of the patient to achieve radiotherapy and/or imaging.

In some embodiments, the radiotherapy target device may include a target component and a housing surrounding the target component. The target component may include a target body and a support supporting the target body. The housing may include a first surface and a second surface allowing radiation beams to pass through. Accordingly, the housing may form a sealed cavity, making the target body work in a closed environment. When electron beams emitted by the electron generating device hit the target body, since the sealed cavity is an oxygen-free or oxygen-poor environment, generation of oxidizing substances may be reduced. In addition, even if an oxidation reaction of the target body produces a small amount of oxidizing substances, the housing can prevent the oxidizing substances from sputtering out of the housing and being deposited on an output window of an accelerating tube, thereby ensuring usability of the accelerating tube, extending service life of the target body and the accelerating tube, and reducing cost.

In some embodiments, the radiotherapy target device may include a target component including a target body and a support supporting the target body. The support may include a flow channel. A first end of the flow channel may be connected with a cavity formed by the support. A second end of the flow channel may be connected with outside of the support. Accordingly, through the flow channel, the oxidizing substances generated by the target body at high temperature may be removed out of the cavity, which can prevent the oxidizing substances from being deposited on the output window, ensure usability of the accelerating tube, extend service life of the target body and the accelerating tube, and reduce cost.

FIG. 1 is a schematic diagram illustrating a cross-sectional structure of an exemplary radiotherapy target device according to some embodiments of the present disclosure. As shown in FIG. 1, the radiotherapy target device 100 may include a target component 110 and a housing 120.

In some embodiments, the target component 110 may include a target body 112 and a support 111. The support 111 may be used to support the target body 112.

In some embodiments, the housing 120 may be located outside the target component 110 and may be used to surround the target component 110. In some embodiments, the housing 120 may be a box-like structure, a cylindrical structure, or any other regular-shaped or irregular-shaped structure. In some embodiments, the housing 120 may form a sealed cavity (e.g., "A" shown in FIG. 5). In some embodiments, the housing 120 may be a partially open structure (e.g., a housing coving the target component 110 or the target body 112) or not totally sealed with outside or not totally in a vacuum state. In some embodiments, the housing 120 may include a first surface 121 and a second surface 122. The first surface 121 and the second surface 122 may be respectively located on both sides of the target body 112 along a beam direction of radiation beams (e.g., "X" direction shown in FIG. 1) and used for the radiation beams to pass through. Specifically, when the radiation beams generated by an electron beam is irradiated on the first surface 121 of the housing 120, the radiation beams may hit the target body 112 through at least a part (e.g., a first window 123 shown in FIG. 5) of the first surface 121 of the housing 120. The target body 112 may convert the radiation beams generated by the electron beam into X-rays and then the X-rays may exit through at least a part (e.g., a second window 124 shown in FIG. 5) of the second surface 122 of the housing 120. More descriptions regarding the housing 120 may be found elsewhere in the present disclosure (e.g., FIG. 5 and descriptions thereof).

In some embodiments, the support 111 may include a target substrate 1111 and a target seat 1112. In some embodiments, the target substrate 1111 may include a through hole 11111 along the beam direction of the radiation beams (e.g., "X" direction shown in FIG. 1). The target seat 1112 may be mounted in the through hole 11111 and used to mount the target body 112.

In some embodiments, the target substrate 1111 may be fixedly connected with the housing 120. In some embodiments, at least one surface of the target substrate 1111 may be fixedly arranged inside the housing 120. There may be a certain space between remaining surfaces of the target substrate 1111 and an inner wall of the housing 120. Accordingly, the target substrate 1111 may be reliably fixed in the housing 120 to prevent the target component 110 from moving. An exemplary fixed connection mode may include a screw connection, a magnetic suction connection, a bonding, a rivet connection, a buckle connection, etc. In some embodiments, the target substrate 1111 may be supported by metal materials.

In some embodiments, the target seat 1112 may be detachably connected to the target substrate 1111. An exemplary detachable connection may include a welding connection, a buckle connection, a magnetic suction connection, etc.

In some embodiments, the target seat 1112 may be non-detachably connected to the target substrate 1111. For example, the target seat 1112 and the target substrate 1111 may be manufactured by integral molding. As another example, the target seat 1112 may be fixedly connected to the target substrate 1111. An exemplary fixed connection mode may include a welding connection, a bonding connection, a screw connection, etc.

In some embodiments, as described in connection with FIGS. 1-3, the target seat 1112 may include a mounting groove 11121 with an opening facing the first surface 121 and a concave part 11122 with an opening facing the second surface 122. The mounting groove 11121 may be used to mount the target body 112. The concave part 11122 may be used to allow X-rays generated by the target body 112 to pass through. In some embodiments, an inner diameter of a side of the concave part 11122 close to the mounting groove 11121 may be smaller than an inner diameter of a side of the concave part 11122 away from the mounting groove 11121.

Figure 2:
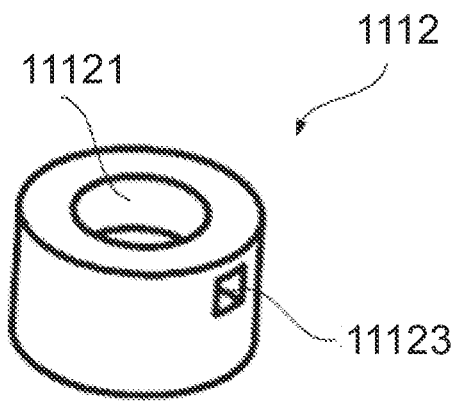
FIG. 2 is a schematic diagram illustrating a structure of an exemplary target seat according to some embodiments of the present disclosure.
Figure 3:
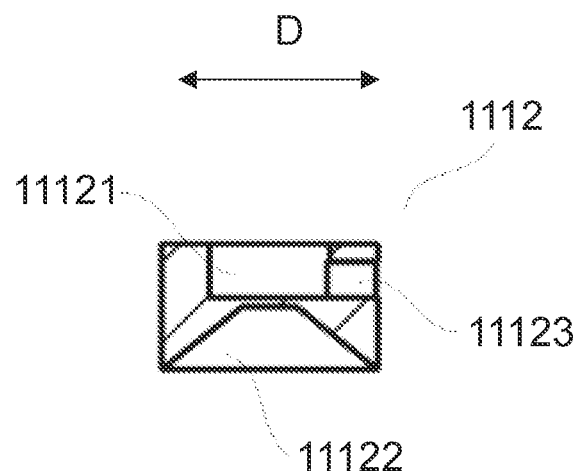
FIG. 3 is a cross-sectional view illustrating an exemplary target seat according to some embodiments of the present disclosure.

In some embodiments, merely by way of example, as shown in FIG. 2 and FIG. 3, a shape of the target seat 1112 may be cylindrical. Accordingly, a cylindrical mounting groove 11121 may be arranged on an end surface of one end of the target seat 1112. The concave part 11122 may be arranged on an end surface of the other end of the target seat 1112. In some embodiments, shapes of the target seat 1112 and/or the mounting groove 11121 may be other shapes, such as a prismatic shape.

In some embodiments, as shown in FIG. 2 and FIG. 3, an outer wall of the target seat 1112 may be opened with a cooling groove 11123. In some embodiments, an extension direction of the cooling groove 11123 may be parallel to a diameter direction of the target seat 1112 (e.g., "D" shown in FIG. 3). In some embodiments, the extension direction of the cooling groove 11123 may be inclined at a certain angle relative to the diameter direction of the target seat 1112. In some embodiments, one end of the cooling groove 11123 may be connected with the mounting groove 11121. The other end may be connected with a cooling component 130. More descriptions of the cooling component 130 may be found elsewhere in the present disclosure (e.g., FIG. 6 and the descriptions thereof).

In some embodiments, a depth of the mounting groove 11121 may be slightly larger than a height of the target body 112. In some embodiments, the depth of the mounting groove 11121 may be less than or equal to the height of the target body 112.

In some embodiments, the target seat 1112 may also include a fixed edge 11124. A fixed groove 11112 may be arranged in the through hole 11111 of the target substrate 1111. The fixed groove 11112 may be used to mount the fixed edge 11124 to mount the target seat 1112 in the through hole 11111.

In some embodiments, the support 111 may also include a target holder 1113, so that the target body 112 may be reliably fixed in the target seat 1112. In some embodiments, the target holder 1113 may be arranged at an end of the target seat 1112 facing the first surface 121 of the housing 120. In some embodiments, the target holder 1113 may be arranged in the mounting groove 11121 of the target seat 1112.

In some embodiments, an accommodating space (e.g., "B" shown in FIG. 1) may be formed between an outer wall of the target seat 1112 and an inner wall of the through hole 11111. The accommodating space may allow the cooling component 130 or a cooling medium to pass through. For example, the cooling component 130 may be directly arranged in the accommodating space, or the cooling medium (e.g., water, liquid nitrogen) may be passed into the accommodating space. More descriptions regarding the cooling component 130 and the cooling medium may be found elsewhere in the present disclosure (e.g., FIG. 6 and descriptions thereof).

In some embodiments, the through hole 11111 may include a first stepped hole 11113 and a second stepped hole 11114 coaxially arranged. An outer wall of the target seat 1112 may be in contact with an inner wall of one of the first stepped hole 11113 and the second stepped hole 11114. The outer wall of the target seat 1112 and an inner wall of the other one of the first stepped hole 11113 and the second stepped hole 11114 may be enclosed as the accommodating space. In this embodiment, leak tightness between the target seat 1112 and the through hole 11111 can be ensured by making the outer wall of the target seat 1112 in contact with the inner wall of the second stepped hole 11114, so as to prevent the radiation beams from passing through a gap between the target seat 1112 and the first stepped hole 11113 and/or the second stepped hole 11114.

In some embodiments, the first stepped hole 11113 may be close to the first surface 121 of the housing 120; the second stepped hole 11114 may be close to the second surface 122 of the housing 120. The outer wall of the target seat 1112 may be in contact with the inner wall of the second stepped hole 11114. The outer wall of the target seat 1112 and the inner wall of the first stepped hole 11113 may be enclosed as the accommodating space. In this situation, a diameter of the first stepped hole 11113 may be larger than a diameter of the second stepped hole 11114.

In some embodiments, the diameter of the first stepped hole 11113 may be in a range of 15 mm~40 mm. In some embodiments, the diameter of the first stepped hole 11113 may be in a range of 30 mm~70 mm. In some embodiments, the diameter of the first stepped hole 11113 may be in a range of 50 mm~100 mm.

In some embodiments, the diameter of the second stepped hole 11114 may be in a range of 10 mm~30 mm. In some embodiments, the diameter of the second stepped hole 11114 may be in a range of 20 mm~60 mm. In some embodiments, the diameter of the second stepped hole 11114 may be in a range of 50 mm~100 mm.

In some other embodiments, The first stepped hole 11113 may be close to the second surface 122 of the housing 120. The second stepped hole 11114 may be close to the first surface 121 of the housing 120. The outer wall of the target seat 1112 may be in contact with the inner wall of the first stepped hole 11113. The outer wall of the target seat 1112 and the inner wall of the second stepped hole 11114 may be enclosed as the accommodating space. In this situation, the diameter of the first stepped hole 11113 may be smaller than the diameter of the second stepped hole 11114.

In some embodiments, the first stepped hole 11113 and/or the second stepped hole 11114 may be a circular hole, a conical hole, or any other regular or irregular shape.

Figure 4:
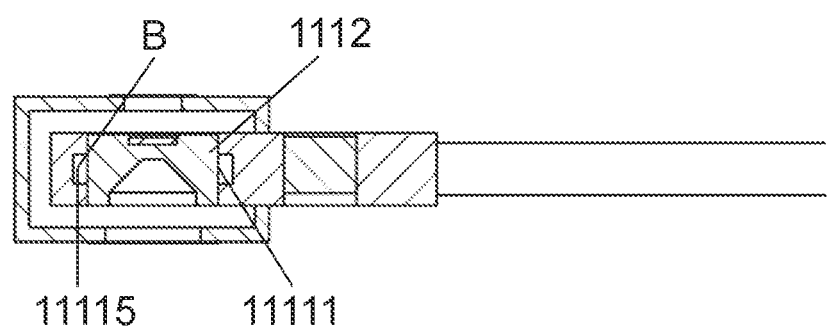
FIG. 4 is a schematic diagram illustrating a cross-sectional structure of an exemplary target seat according to other embodiments of the present disclosure.

In some embodiments, as shown in FIG. 4, a first slot 11115 may be arranged in an inner wall of the through hole 11111. Accordingly, the accommodating space "B" may be enclosed by an inner wall of the first slot 11115 and an outer wall of the target seat 1112. In some embodiments, the first slot 11115 may include a plurality of first slots. The plurality of first slots 11115 may be distributed along a central axis of the through hole 11111 at an interval. In some embodiments, a cross-sectional shape of the first slot 11115 may be a rectangle, a semicircle, an ellipse, a trapezoid, etc.

In some embodiments, a second slot (not shown) may be arranged in an outer wall of the target seat 1112. Accordingly, the accommodating space "B" may be enclosed by the second slot and an inner wall of the through hole 11111. In some embodiments, the second slot may also include a plurality of second slots. The plurality of second slots may be distributed along the outer wall of the target seat 1112.

In some embodiments, the accommodating space "B" may be enclosed by the first slot 11115, the second slot, the outer wall of the target seat 1112, and the inner wall of the through hole 1111.

Figure 13:
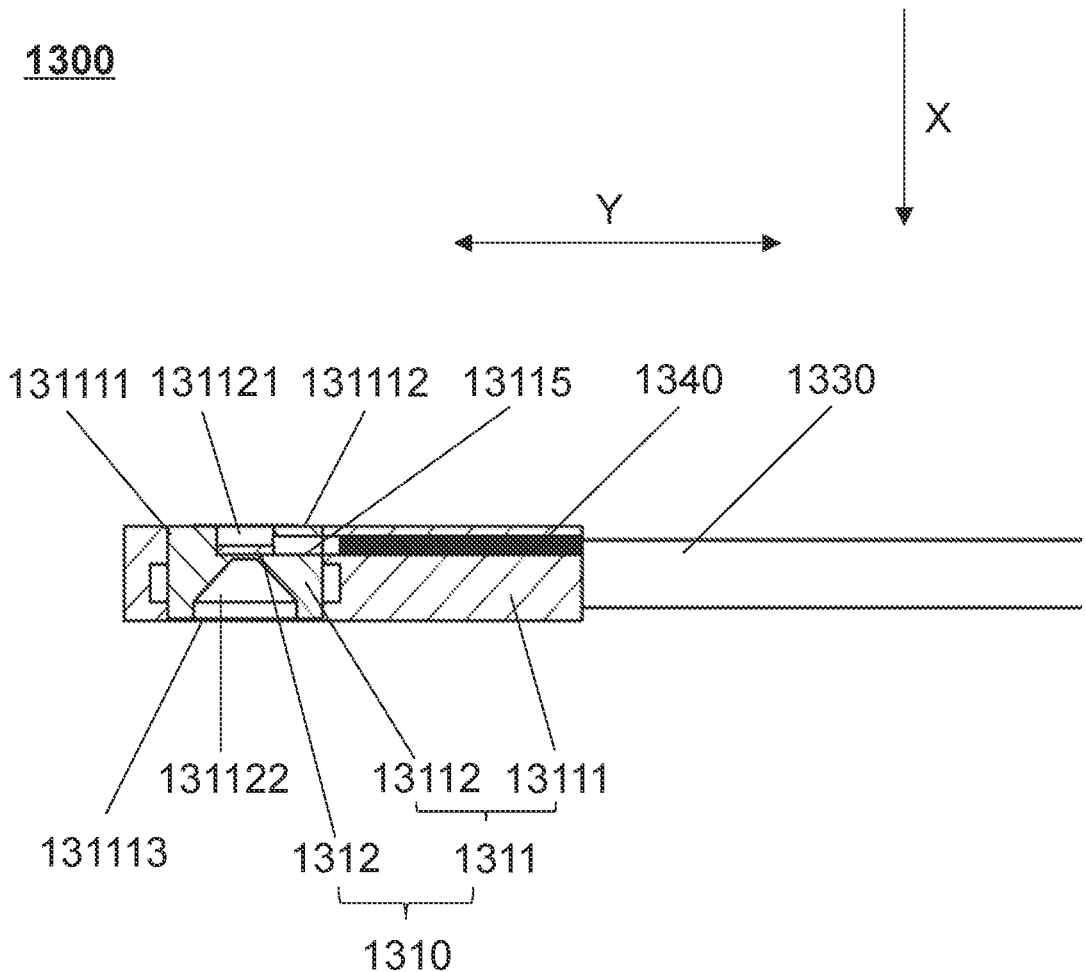
FIG. 13 is a schematic diagram illustrating an exemplary radiotherapy target device provided with a flow channel according to some embodiments of the present disclosure.

In some embodiments, the support 111 may also include a flow channel (e.g., a flow channel 13115 shown in FIG. 13). In some embodiments, a first end of the flow channel may be connected with a cavity formed within the support 111, a second end of the flow channel 111 may be connected with outside of the support 111. The flow channel may be used to discharge oxidizing substances generated by the target body 112. For example, if the housing 120 is a partially open structure or not totally sealed with outside or not totally in a vacuum state, some oxidizing substances may be generated by the target body 112 and may be discharged outside of the housing 120 or the target body 112.

In some embodiments, the second end of the flow channel may be connected with an inert-gas source or a vacuum component. When the second end of the flow channel is connected with the inert-gas source, inert gas may be delivered to the cavity of the support 111 through the flow channel. The inert gas can make the target body 112 operate in an environment formed by the inert gas, preventing the target body 112 from contacting with oxygen, so that an oxidation reaction may not occur at high temperature to generate oxidizing substances. When the second end of the flow channel is connected with the vacuum component, oxygen in the cavity may be extracted through the vacuum component, so that the cavity may be kept in vacuum and the target body 112 can be prevent from contacting with oxygen to cause an oxidation reaction. More descriptions regarding the flow channel may be found elsewhere in the present disclosure (e.g., FIGS. 13-20 and descriptions thereof).

In some embodiments, the target component 110 may also include an adsorption component (e.g., an adsorption component 1340 shown in FIG. 13). In some embodiments, the adsorption component may be arranged in the flow channel and/or an inner surface of the housing 120. The adsorption component may be used to adsorb oxygen, so that the target body 112 can be prevent from contacting with oxygen to cause an oxidation reaction. For example, if the housing 120 is a partially open structure or not totally sealed with outside or not totally in a vacuum state, the adsorption component may be used to adsorb oxygen in the housing 120. More descriptions regarding the adsorption component may be found elsewhere in the present disclosure (e.g., FIG. 13, FIG. 14, FIG. 17 and descriptions thereof).

Figure 5:
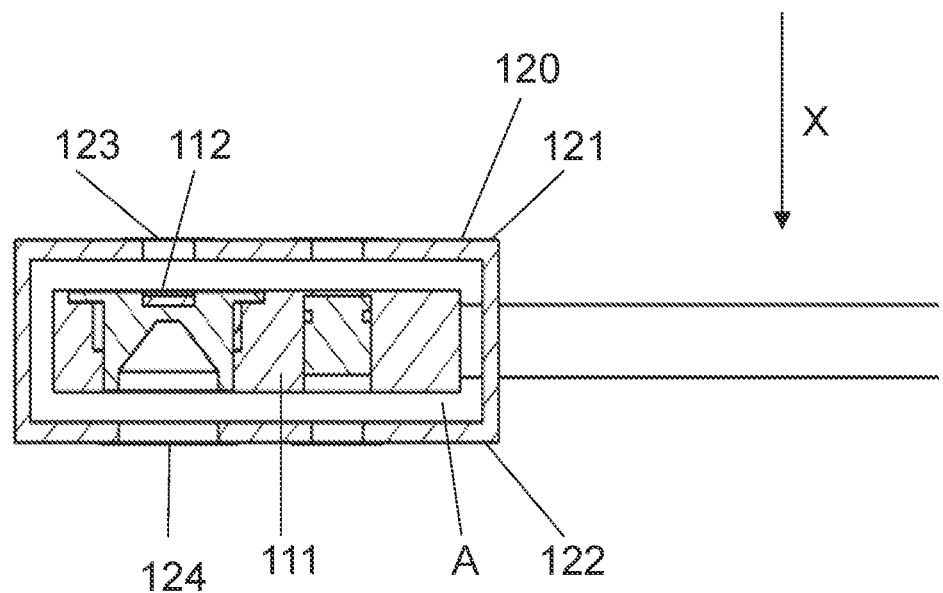
FIG. 5 is a cross-sectional view illustrating an example radiotherapy target device according to some embodiments of the present disclosure.

In some embodiments, as shown in FIG. 5, the housing 120 may include a first window 123 and a second window 124 respectively arranged on the first surface 121 and the second surface 122. The first window 123 and the second window 124 may be used to allow the radiation beams to pass through. In some embodiments, the first window 123 and the second window 124 may be located on both sides of the target body 112 and at least partially correspond to each other. In some embodiments, a central axis of the first window 123 and a central axis of the second window 124 may coincide or a difference thereof is less than a predetermined threshold (e.g., 1 mm, 2 mm, 3 mm, 5 mm).

In some embodiments, in order to allow the radiation beams to successfully hit the target body 112 through the first window 123, a size (or a cross-sectional area) of the first window 123 may need to meet a certain requirement. In some embodiments, the size of the first window 123 may be in a range of 5 mm to 5 cm. In some embodiments, the size of the first window 123 may be in a range of 2 mm to 2 cm. In some embodiments, the size of the first window 123 may be in a range of 5 mm to 1 cm.

In some embodiments, since X-rays generated by the target body 112 are divergent, a size (or a cross-sectional area) of the second window 124 needs to meet a certain requirement, so as to ensure that the radiation beams can be emitted from the second window 124 as much as possible after being converted into X-rays. In some embodiments, the size (or the cross-sectional area) of the second window 124 may be larger than the cross-sectional area of the first window 123.

In some embodiments, the size of the second window 124 may be in a range of 7.5 mm~15 mm. In some embodiments, the size of the second window 124 may be in a range of 10 mm~20 mm. In some embodiments, the size of the second window 124 may be in a range of 20 mm~50 mm.

It should be noted that the "size" described in the present disclosure may refer to a size in a broad sense. For example, if the cross section of the window is a circle, the size may refer to a diameter of the circle. As another example, if the cross section of the window is a square, the size may refer to a side length or a diagonal length of the square. As another example, if the cross section of the window is a triangle, the size may refer to a side length or a centerline length of the triangle. As yet another example, if the cross section of the window is a polygon, the size may refer to a length of any side of the polygon or a diameter of a circle formed by the polygon. In other words, "size" may refer to any parameter that can characterize the cross-sectional area of the window, which may not be limited in the present disclosure.

In some embodiments, a first through mounting hole (not shown) may be arranged on the first surface 121. A second through mounting hole (not shown) may be arranged on the second surface 122. Accordingly, the first window 123 and the second window 124 may be mounted in the first mounting hole and the second mounting hole, respectively, by a sealing mode (e.g., welding and sealing mounting with a seal).

In some embodiments, materials of the first window 123 and/or the second window 124 may include, but are not limited to beryllium, stainless steel, titanium, copper, or other materials that can allow X-rays to pass through. In some embodiments, the materials of the first window 123 and/or the second window 124 may be the same as or different from materials of other parts of the housing 120. If both the first window 123 and the second window 124 are made of the same material as the other parts of the housing 120, an output window of an accelerating tube may be directly aligned with the target body 112, and there may be no need to additionally adjust a position of the output window, which can simplify the operation process.

In some embodiments, a thickness of the first window 123 may be less than 100 microns. In some embodiments, the thickness of the first window 123 may be less than 75 microns. In some embodiments, the thickness of the first window 123 may be less than 50 microns.

In some embodiments, a thickness of the second window 124 may be less than 100 microns. In some embodiments, the thickness of the second window 124 may be less than 75 microns. In some embodiments, the thickness of the second window 124 may be less than 50 microns.

In some embodiments, the housing 120 may also include a hole. In some embodiments, the hole may be a through hole (not shown). In some embodiments, the through hole may be connected to the outside environment. In some embodiments, the through hole may be connected with an inert-gas source or a vacuum component to discharge air in the housing 120 or a sealed cavity (e.g., "A" shown in FIG. 5) or supply inert gas to the housing 120 or the sealed cavity so that the housing 120 or the sealed cavity may be kept in a vacuum or oxygen-free state. In some embodiments, the housing 120 may also include no through hole, and the vacuum or oxygen-free state of the housing 120 or the sealed cavity "A" may be achieved directly by means of vacuum assembly.

In some embodiments, the radiotherapy target device 100 may also include the cooling component 130 mentioned above. The cooling component 130 may pass through the housing 120 and may be partially located inside the housing 120. The cooling component 130 may be used to cool the target component 110. In some embodiments, a part of the cooling component 130 may be located inside the support 111. In some embodiments, the cooling component 130 may be arranged on a peripheral side of the target body 112 (e.g., surrounding the target body 112) to cool the target body 112.

Figure 6:
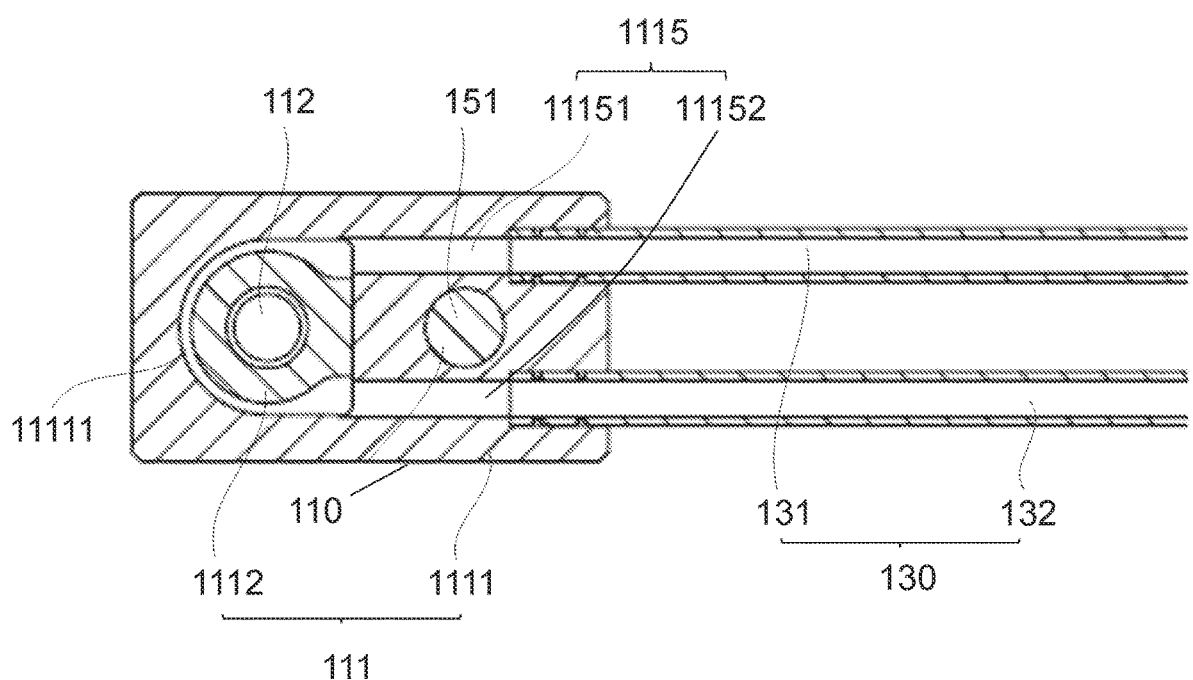
FIG. 6 is a schematic diagram illustrating an exemplary assembly relationship between a cooling component and a target substrate according to some embodiments of the present disclosure.
Figure 7:
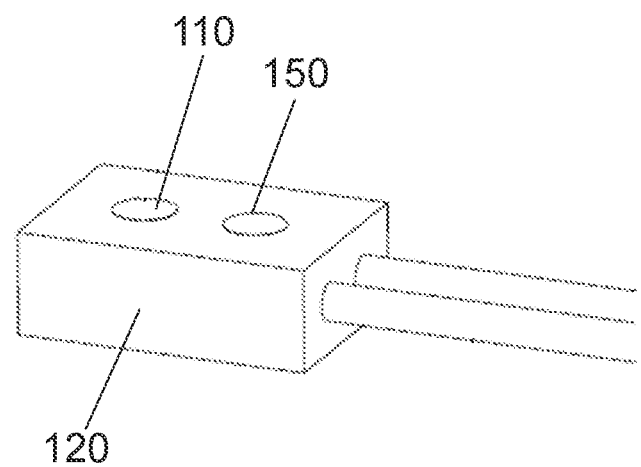
FIG. 7 is a schematic diagram illustrating a structure of an exemplary second target component according to some embodiments of the present disclosure.
Figure 8:
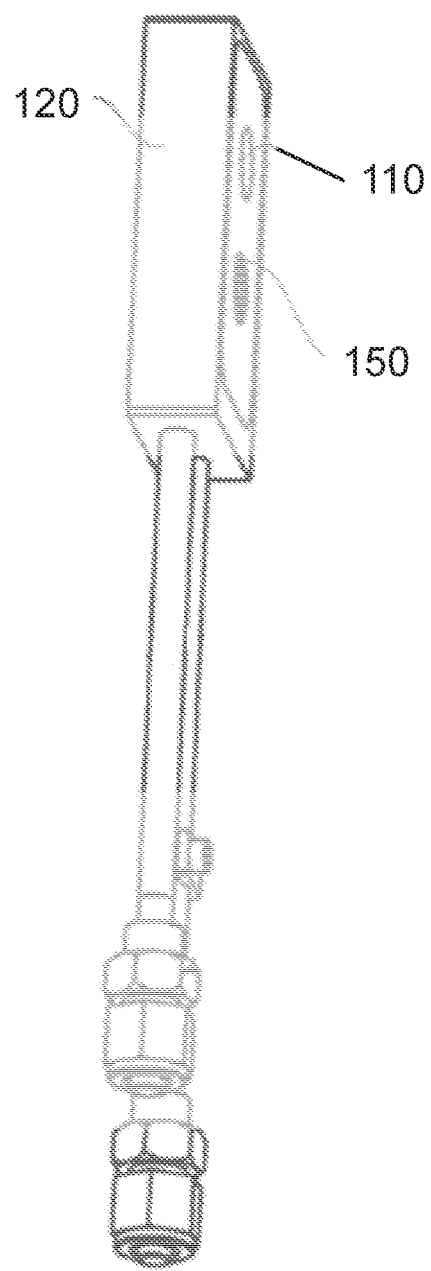
FIG. 8 is a schematic diagram illustrating a structure of an exemplary second target component according to yet other embodiments of the present disclosure.
Figure 9:
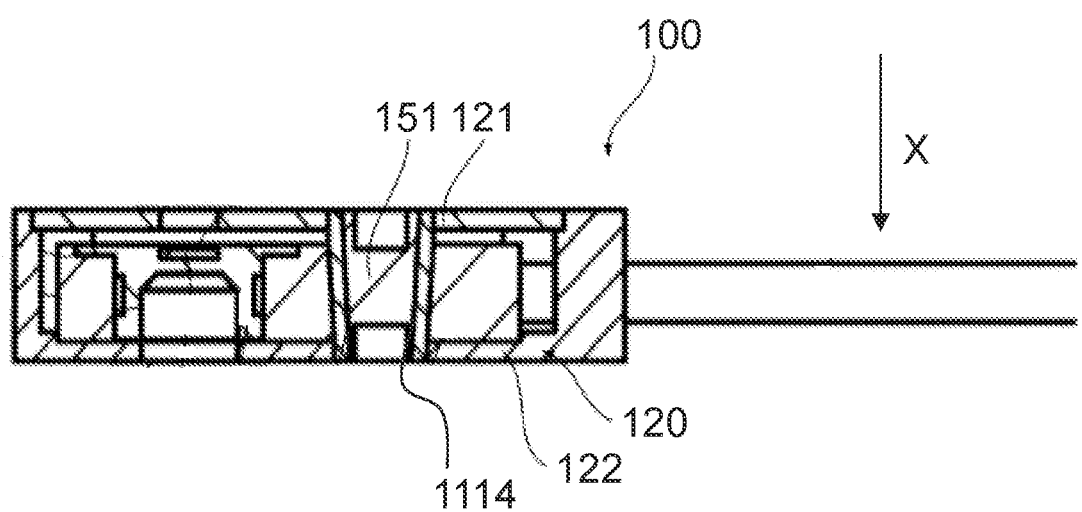
FIG. 9 is a schematic diagram illustrating a cross-sectional structure of an exemplary radiotherapy target device according to some embodiments of the present disclosure.
Figure 10:
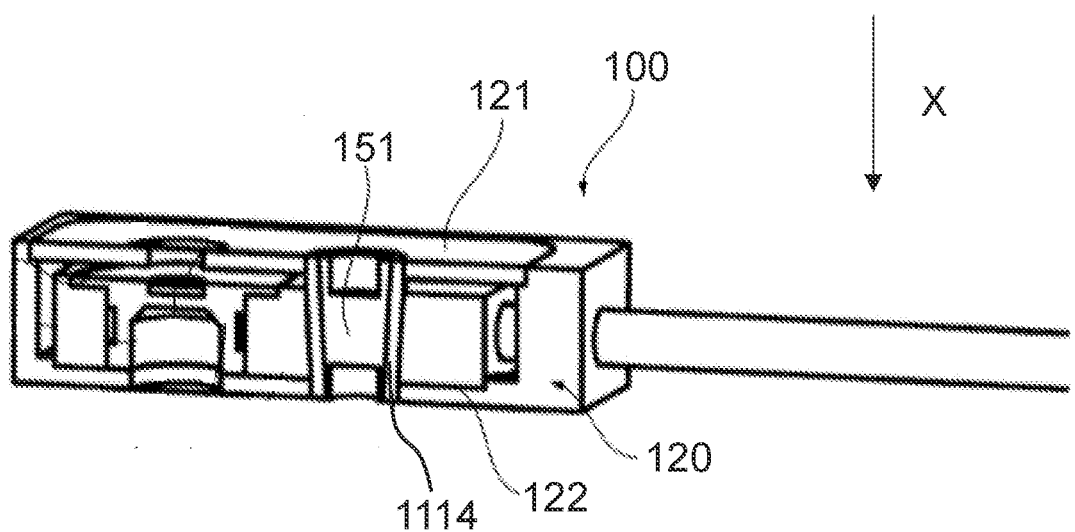
FIG. 10 is a schematic diagram illustrating a cross-sectional structure of an exemplary radiotherapy target device according to some embodiments of the present disclosure.

In some embodiments, as shown in FIG. 6, the cooling component 130 may include a cooling inlet pipe 131 and a cooling outlet pipe 132. The cooling medium may be delivered into the support 111 through the cooling inlet pipe 131. The cooling medium in the support 111 may be discharged through the cooling outlet pipe 132.

In some embodiments, the support part 111 may include a cooling channel 1115. In some embodiments, a part of the cooling channel 1115 may enclose the peripheral side of the target body 112 or the target seat 1112. In some embodiments, the cooling channel 1115 may include a channel inlet 11151 and a channel outlet 11152. The cooling inlet pipe 131 may connect with an output end of an external cooling source and the channel inlet 11151. The cooling outlet 132 may connect with an input end of the external cooling source and the channel inlet 11152. Specifically, the output end of the external cooling source deliver cooling liquid into the cooling inlet pipe 131, and into the cooling channel 1115 through the channel inlet 11151. The cooling liquid may absorb heat generated by the target body 112, and then be delivered to the input end of the external cooling source through the channel outlet 11152. Finally, the cooling liquid may be cooled by the external cooling source to achieve recycling of the cooling liquid. In some embodiments, the cooling liquid absorbing the heat may also be directly discharged to an external environment through the cooling outlet pipe 11152.

In some embodiments, the cooling component 130 may be arranged directly in the cooling channel 1115. For example, the cooling component 130 may include a cooling pipe, and the cooling pipe may include an inlet end and an outlet end. The cooling pipe may be arranged in the cooling channel 1115 and may enclose the peripheral side of the target body 112 or the target seat 1112. The inlet end of the cooling pipe may be connected to the output end of the external cooling source. The outlet end of the cooling pipe may be connected to the input end of the external cooling source.

In some embodiments, the cooling component 130 and the housing 120 may be hermetically connected. A sealed cavity may be formed inside the housing 120 through the hermetical connection. An exemplary hermetical connection may include a welding connection, a sealant sealing, etc.

In some embodiments, the cooling component 13 may support the support 111 on the housing 120, so that the support 111 may be not in contact with the inner wall of the housing 120. For example, the cooling component 130 may be connected to the housing 120 and the support 111, respectively, so that the support 111 may be suspended inside the housing 120. In some embodiments, after the cooling component 13 is connected to the support 111, at least one surface of the support 111 may be brought into contact with or connected to the housing 120.

In some embodiments, as shown in FIG. 1 and FIGS. 7-12, the radiotherapy target device 100 may also include a second target component 150. In this situation, the target component 110 can be also be referred to as a "first target component." In some embodiments, the second target component 150 may include a second target body 151 (also can be considered that the second target component 150 includes the second target body 151 and the support 111). The support 111 may also include a second target seat 1114. The second target seat 1114 may be used to mount the second target body 151. In some embodiments, the second target seat 1114 may include a placement groove. The placement groove may be used to place the second target body 151. In some embodiments, taking FIG. 9 and FIG. 10 as an example, the first surface 121 and the second surface 122 of the housing 120 may be provided with a first hole and a second hole, respectively. The target substrate 1111 may include a second through hole along a beam direction of the radiation beams ("X" shown in FIG. 9). The first hole and the second hole may be located on both sides of the second through hole along a beam direction of the radiation beams, and may be coaxially arranged with the second through hole. The second target seat 1114 may be hollow. A part of the second target body 151 may be located inside the second target seat 1114, and the other part may be exposed to the housing 120.

In some embodiments, the second target seat 1114 may be mounted in the second through hole in a sealing mode, so that an outer wall of the second target seat 1114 and an inner wall of the first hole and an inner wall of the second hole may be enclosed as a sealed cavity.

Figure 11:
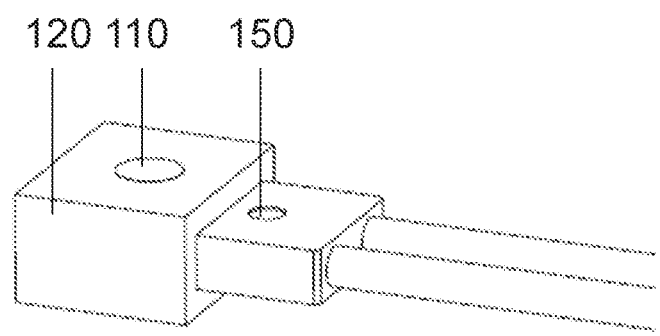
FIG. 11 is a schematic diagram illustrating an exemplary second target component according to other embodiments of the present disclosure.
Figure 12:
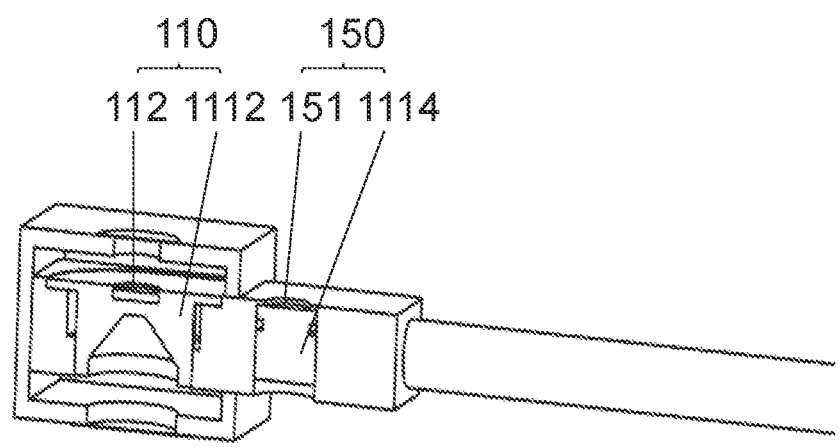
FIG. 12 is a schematic diagram illustrating an exemplary second target component according to yet other embodiments of the present disclosure.

In some embodiments, as shown in FIG. 1 and FIGS. 7-12, the second target body 151 may be located inside or outside the housing 120. For example, as shown in FIG. 1 and FIGS. 7-10, the second target body 151 may be located inside the housing 120 (e.g., inside the sealed cavity formed by the housing 120). As another example, as shown in FIG. 11 and FIG. 12, the second target body 151 may be located outside the housing 120 (e.g., outside the sealed cavity formed by the housing 120).

In some embodiments, when the second target component 150 is located inside the housing 120, the target component 110 may be used for radiotherapy and the second target component 150 may be used for imaging.

In some embodiments, at least part of the second target seat 1114 is sealed with the housing 120 and the second target body 151 is located outside of the sealed cavity formed by the housing 120. For example, as shown in FIG. 12, the second target seat 1114 passes through a side wall of the housing 120 and is sealed with the side wall of the housing 120. The first target seat 1112 (used for mounting the target body 112) is located at the inner end of the housing 120 and the second target seat 1114 (used for mounting the second target body 151) is located at the outer end of the housing 120. In some embodiments, an sealed connection mode may include a welding, a bonding, an integrated molding, etc.

In some embodiments, as described in connection with FIG. 6, the cooling channel 1115 may enclose a peripheral side of the second target body 151 to cool the second target body 151.

In some embodiments, the target component 110 may be different from the second target component 150. In some embodiments, the target component 110 may be a high-energy target component (e.g., a tungsten target). The second target component 150 may be a low-energy target component (e.g., a copper target, an aluminum target, a graphite target).

In some embodiments, the high-energy target component and the low-energy target component may be distinguished based on an energy threshold. In some embodiments, the energy threshold may be in a range of 4 MeV~7 MeV. In some embodiments, the energy threshold may be in a range of 6 MeV~10 MeV. In some embodiments, the energy threshold may be in a range of 10 MeV~24 MeV.

In some embodiments, the high-energy target component and the low-energy target component may be distinguished based on a radiation power threshold. In some embodiments, the radiation power threshold may be in a range of 0.5 kW~1.5 kW. In some embodiments, the radiation power threshold may be in a range of 1 kW~3 kW.

In some embodiments, the radiotherapy target device 100 may also include more target components, such as three, four, five target components, etc.

FIG. 13 is a schematic diagram illustrating an exemplary radiotherapy target device provided with a flow channel according to some embodiments of the present disclosure. As shown in FIG. 13, the radiotherapy target device 1300 may include a target component 1310. The target component 1310 may include a support 1311 and a target body 1312. The support 1311 may be used to support the target body 1312.

In some embodiments, the support 1311 may include a target substrate 13111 and a target seat 13112. In some embodiments, the target seat 13112 may be arranged on the target substrate 13111 and may be arranged inside a cavity formed inside the support 1311.

In some embodiments, the target substrate 13111 may include a through hole 131111 along a beam direction of radiation beams (e.g., "X" shown in FIG. 13). The target seat 13112 may be mounted in the through hole 131111 and used to mount the target body 1312.

Figure 14:
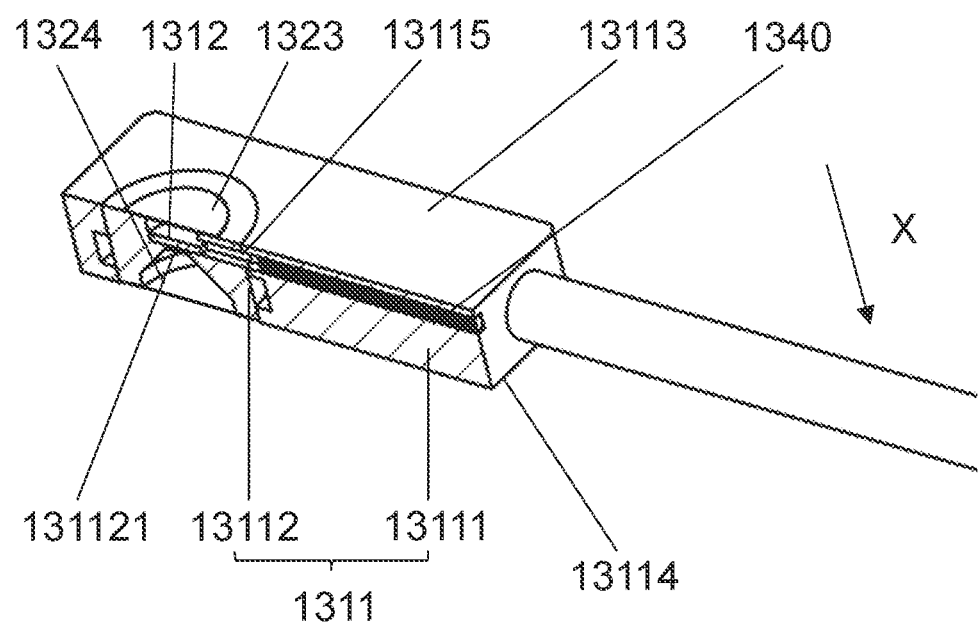
FIG. 14 is a cross-sectional view of the radiotherapy target device shown in FIG. 13 at another angle.

In some embodiments, the target substrate 131111 may include a first surface 131112 and a second surface 131113 arranged opposite to each other. The first surface 131112 and the second surface 131113 may be located on both sides of the target substrate 1311 along the beam direction of the radiation beams. In some embodiments, as shown in FIG. 14, the support 1311 may also include a first cover plate 13113 and a second cover plate 13114, which may be respectively covered on the first surface 131112 and the second surface 131113. In some embodiments, the structure of the target substrate 13111 may be similar to or the same as that of the target substrate 1111. More details may be found in FIG. 1 and descriptions thereof.

In some embodiments, the target seat 13112 may include a mounting groove 131121 with an opening facing the first surface 131112 and a concave part 131122 with an opening facing the second surface 131113. The mounting groove 131121 may be used to mount the target 1312. The concave part 131122 may be used to allow the radiation beams to pass through. In some embodiments, the first cover plate 13113 may be used to seal the mounting groove 131121. The second cover plate 13114 may be used to seal the concave part 131122. Accordingly, the first cover plate 13113 and the second cover plate 13114 may prevent oxidizing substances generated by the target body 1312 from sputtering onto the output window of an accelerating tube. In some embodiments, the structure of the target seat 13112 may be similar to or the same as that of the target seat 1112. More details may be found in FIGS. 1-3 and descriptions thereof.

In some embodiments, as described in connection with FIG. 14 and FIG. 16, a first window 1323 may be arranged on the first cover plate 13113. The first window 1323 may correspond to a position of the target body 1312. The first window 1323 may allow the radiation beams to pass through. A second window 1324 may be arranged on the second cover plate 13114. The second window 1324 may correspond to a position of the target body 1312. The second window 1323 may allow X-rays to pass through. In some embodiments, the first window 1323 and the second window 1324 may be the same as or similar to the first window 123 and the second window 124. More details may be found in FIG. 5 and descriptions thereof.

In some embodiments, the support 1311 may also include a flow channel 13115. In some embodiments, a first end of the flow channel 13115 may be connected with a cavity formed by the support 1311. A second end may be connected with outside of the support 1311. In some embodiments, the flow channel 13115 may be connected with an inert-gas source or a vacuum component.

In some embodiments, an extension direction of the flow channel 13115 may be perpendicular to a beam direction (e.g., "X" shown in FIG. 13) of the radiation beams and parallel to a length direction (e.g., "Y" shown in FIG. 13) of the support 1311. In some embodiments, the flow channel 13115 may also be arranged obliquely with respect to the beam direction of the radiation beams. In some embodiments, the flow channel 13115 may be arranged in a straight line on a horizontal plane. In some embodiments, the flow channel 13115 may be arranged in a curve on the horizontal plane.

In some embodiments, the support 1311 may also include a backflow groove (not shown). In some embodiments, one end of the backflow groove may be connected with a cavity of the support 1311. The other end of the backflow groove may pass through the support 1311, and be connected with an external environment or an inert-gas source. For example, one end of the backflow groove may be connected with the mounting groove 131121 of the target seat 13112. As another example, one end of the backflow groove may be connected with the concave part 131122 of the target seat 13112.

In some embodiments, an arrangement form of the backflow groove may be the same as or similar to an arrangement form of the flow channel 13115. The backflow groove and the flow channel 13115 may be used to achieve different functions respectively. For example, the flow channel 13115 may include a plurality of channels. Some of the flow channels 13115 may be used to connect with an output end of the inert-gas source to deliver inert gas to the cavity of the support 1311. The other flow channels 13115 may be used as backflow grooves to connect with an input end of the inert gas or the external environment.

In some embodiments, the arrangement form of the backflow groove may be different from the arrangement form of the flow channel 13115. For example, the flow channel 13115 may be connected with the inert-gas source. The backflow groove may be connected with the external environment to discharge inert gas. As another example, the flow channel 13115 may be connected with the inert-gas source. The backflow groove may also be connected with the inert-gas source to form a circuit of the flow of inert gas in the target substrate 13111. Specifically, the flow channel 13115 may be connected with the output end of the inert-gas source and the cavity of the target substrate 13111. The backflow groove may be connected with the input end of the inert-gas source and the cavity of the target substrate 13111. The inert gas may be delivered to the cavity of the target substrate 13111 through the flow channel 13115, and then the inert gas may be delivered to the inert-gas source through the backflow groove for processing for subsequent use.

In some embodiments, the flow channel 13115 may be arranged on the target substrate 13111. For example, the flow channel 13115 may be arranged inside the target substrate 13111. As another example, the flow channel 13115 may be arranged on a surface of the target substrate 13111 (e.g., a groove opened on the first surface 131112).

In some embodiments, the flow channel 13115 may be arranged on the first cover plate 13113 and/or the second cover plate 13114. For example, the flow channel 13115 may be arranged inside the first cover plate 13113. As another example, the flow channel 13115 may be arranged on a surface of the first cover plate 13113 facing the target substrate 13111 (e.g., a groove on the surface). As a further example, the flow channel 13115 may be partially arranged on the first surface 131112 of the target substrate 13111 and partially arranged on a surface of the first cover plate 13113 facing the target substrate 13111. Specifically, a part of the groove may be arranged on the first surface 131112 of the target substrate 13111 and a part of the groove may be arranged on the surface of the first cover plate 13113. After the first cover plate 13113 is set on the target substrate 13111, the two grooves are aligned to form the complete flow channel 13115.

Figure 15:
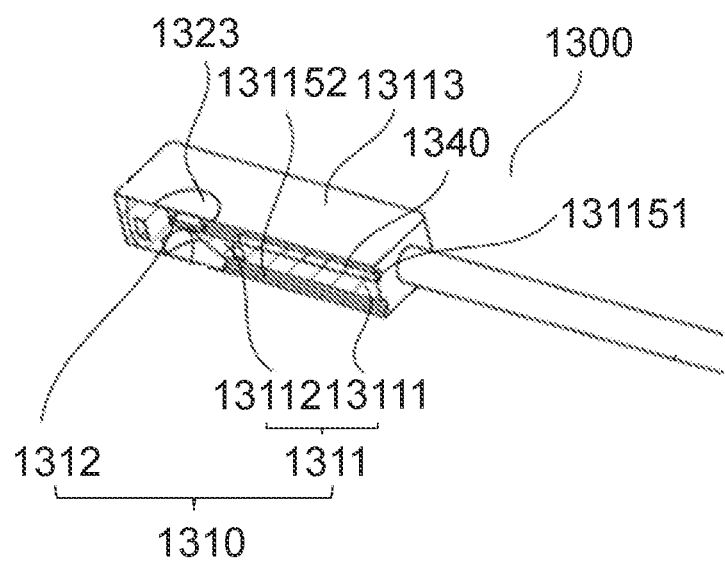
FIG. 15 is a schematic diagram illustrating an exemplary radiotherapy target device provided with two flow channels according to other embodiments of the present disclosure.
Figure 16:
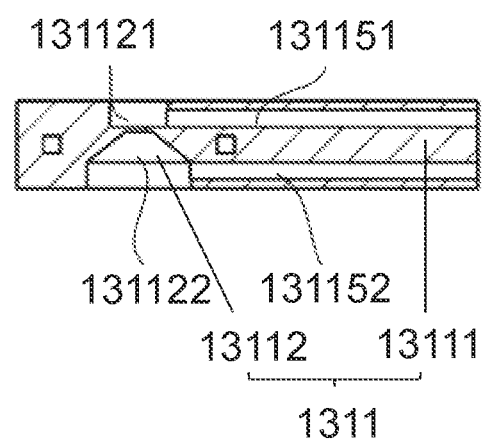
FIG. 16 and FIG. 17 are cross-sectional views of an exemplary radiotherapy target device with two flow channels according to other embodiments of the present disclosure.
Figure 17:
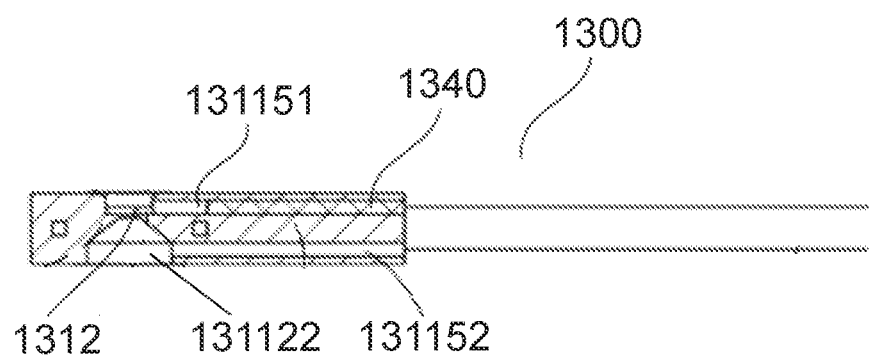

In some embodiments, as shown in FIGS. 15-17, the flow channel 13115 may include a first channel 131151 and a second channel 131152. One end of the first channel 131151 may be connected with the mounting groove 131121 of the target seat 13112. The other end may be connected with outside of the support 1311. One end of the second channel 131152 may be connected with a concave part of the target seat 13112. The other end may be connected with outside of the support 1311.

In some embodiments, an extension direction of the first channel 131151 may be parallel to an extension direction of the second channel 131152.

In some embodiments, both the first channel 131151 and the second channel 131152 may be connected with an external inert-gas source or a vacuum component. In some embodiments, the first channel 131151 and the second channel 131152 may be connected with different devices or components, respectively.

In some embodiments, similar to the flow channel 13115, the backflow groove may include a first backflow groove (not shown) and a second backflow groove (not shown). The first backflow groove may correspond to the first channel 131151. The second backflow groove may correspond to the second channel 131152. In some embodiments, one of the first backflow groove and the second backflow groove may be connected with the external environment. The other backflow groove may be connected with the input end of the inert-gas source. In other embodiments, both the first backflow groove and the second backflow groove may be connected with the external environment or the input end of the inert-gas source.

In some embodiments, the target component 1310 may also include an adsorption component 1340. In some embodiments, merely by way of example, as shown in FIG. 13 and FIG. 14, the adsorption component 1340 may be arranged in the flow channel 13115 for adsorbing oxygen in the flow channel 13115, which can reduce oxygen into the cavity, thereby reducing the generation of oxidizing substances. Even if some oxygen enters the cavity, due to a small amount of oxygen, oxidation substances generated may be deposited on the inner wall of the flow channel 13115 instead of the output window of the accelerating tube.

In some embodiments, a length of the adsorption component 1340 may be 0.2 to 1 times a length of the flow channel 13115. In some embodiments, a length of the adsorption component 1340 may be 0.4~0.8 times a length of the flow channel 13115. In some embodiments, a length of the adsorption component 1340 may be 0.5~0.7 times a length of the flow channel 13115.

In some embodiments, the adsorption component 1340 may be arranged at an edge position or a middle area of the flow channel 13115 to meet adsorption needs of different situations. For example, the adsorption component 1340 may be arranged at one end of the flow channel 13115 away from the target body 1312, which can ensure the effect of adsorbing oxygen and reduce oxygen entering the cavity.

In some embodiments, the adsorption component 1340 may also be arranged in other positions of the target component 1310. For example, the adsorption component 1340 may be directly arranged in the through hole 131111 of the target substrate 131111. As another example, the adsorption component 1340 may be directly arranged in the mounting groove 131121 or the concave part 131122 of the target seat 13112.

In some embodiments, the adsorption component 1340 may include porous adsorption materials (e.g., activated carbon), organic synthetic porous materials (e.g., melamine resin nanoporous carbon materials), antioxidants (e.g., iron powder, titanium powder, phosphorus powder, etc.), or the like, or any combination thereof.

In some embodiments, as another example, both the first channel 131151 and the second channel 131152 may be arranged with the adsorption component 1340. In some embodiments, the adsorption component 1340 may be arranged in one of the first channel 131151 and the second channel 131152.

In some embodiments, the radiotherapy target device 1300 may also include a housing (not shown). The housing may be used to house the target component 1310, and may allow the radiation beams and X-rays to pass through. In some embodiments, a sealed cavity (e.g., "A" shown in FIG. 5) may be formed inside the housing. In some embodiments, the housing, the first cover plate 13113, and the second cover plate 13114 may be independent structures. For example, on the basis of the embodiments shown in FIG. 13, the housing may be arranged outside the first cover plate 13113 and the second cover plate 13114. In some embodiments, the housing may be a component of the support 1311. The first cover plate 13113 and the second cover plate 13114 may be a part of the housing. In some embodiments, the housing may be the same as or similar to the housing 120. More details may be found in FIG. 1, FIG. 5, and descriptions thereof.

In some embodiments, when the radiotherapy target device 1300 includes the housing, the adsorption component 1340 may be arranged in the housing (e.g., on an inner surface of the housing) to adsorb oxygen in the housing, reduce oxygen content inside the housing, and reduce the generation of oxidizing substances. For example, if the housing is a partially open structure or not totally sealed with outside or not totally in a vacuum state, the adsorption component may be used to adsorb oxygen in the housing.

In some embodiments, the radiotherapy target component 1300 may also include a cooling component 1330. As described in other embodiments (e.g., FIG. 6 and embodiments thereof) of the present disclosure, the cooling component 1330 may be used to cool the target body 1312. In addition, when the cooling component 1330 is combined with the flow channel 13115, the cooling component 1330 may also be used to cool the flow channel 13115. In some cases, the oxidizing substances generated by the target body 1312 may flow along the flow channel 13115. If the cooling component 1330 is located on the peripheral side of the flow channel 13115, the oxidizing substances may condense on an inner wall of the flow channel 13115, so as to prevent the oxidizing substances from flowing out of the flow channel 13115 and being deposited on the output window of the accelerating tube, thereby ensuring usability of the accelerating tube.

Figure 18:
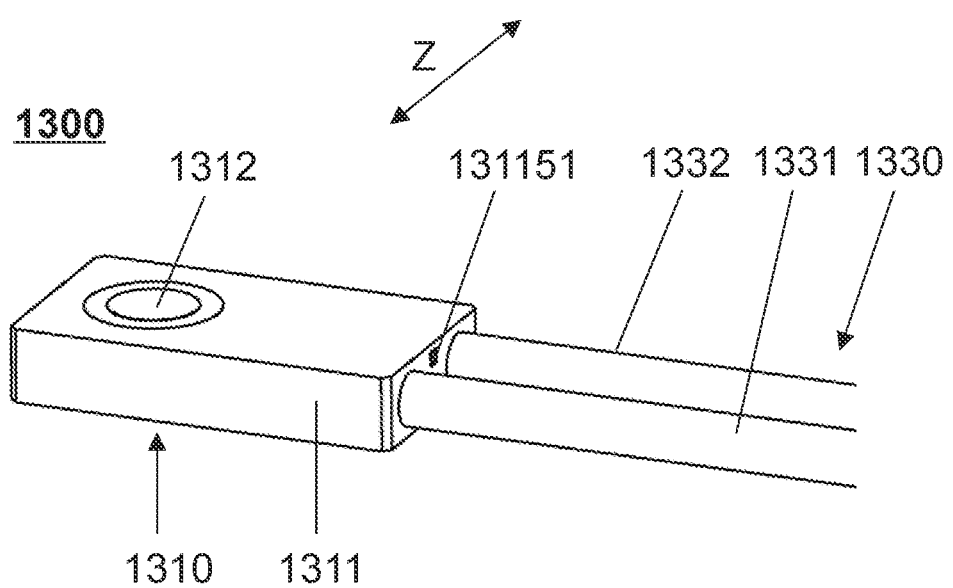
FIGS. 18-20 are schematic diagrams illustrating an exemplary cooling component according to some embodiments of the present disclosure.

In some embodiments, merely by way of example, as shown in FIG. 18, the cooling component 1330 may include a cooling inlet pipe 1331 and a cooling outlet 1332. A part of the cooling outlet pipe 1332 and a part of the cooling inlet pipe 1331 may be located in the support 1311, and may be respectively located on both sides of the first channel 131151 along a width direction (e.g., "Z" shown in FIG. 18) of the support 1311.

Figure 19:
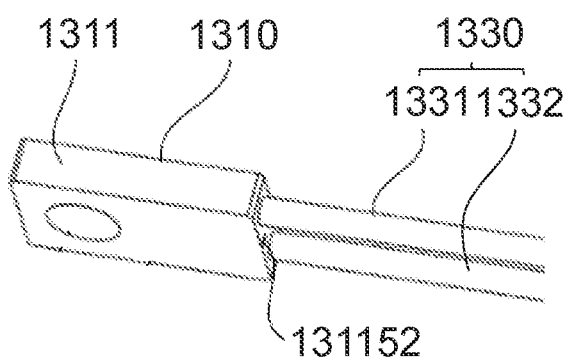

In some embodiments, as another example, as shown in FIG. 19, when the second channel is arranged on the support 1311, the cooling component 1330 can be used to cool the second channel 131152.

Figure 20:
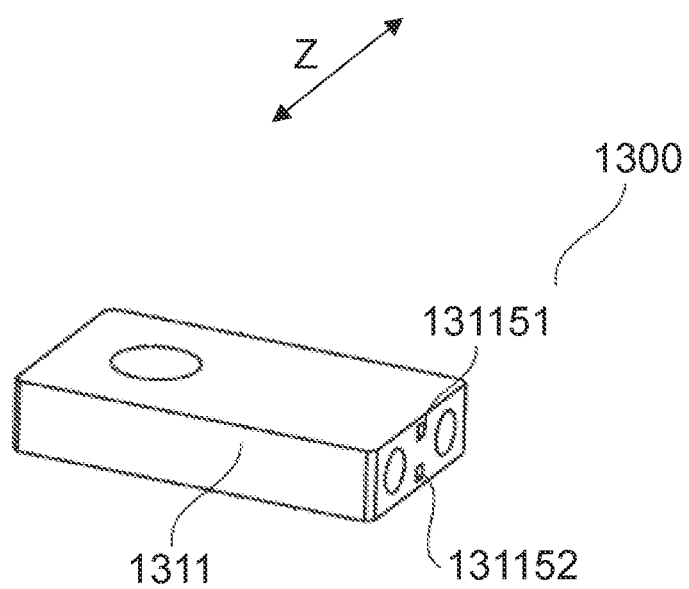

In some other embodiments, as another example, as shown in FIG. 20, when the first channel 131151 and the second channel 131152 are arranged on the support 1311, the cooling component (not shown) may simultaneously cool the first channel 131151 and the second channel 131152.

In some embodiments, a part of the cooling component 1330 located in the support 1311 may be arranged in parallel with the flow channel 13115. In some embodiments, the part of the cooling component 1330 located in the support 1311 may be arranged in a spiral shape around the flow channel 13115. In some embodiments, the cooling component 1330 may be in direct contact with the flow channel 13115 to improve cooling efficiency of the flow channel 13115.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A radiotherapy target device, comprising:
   a target component including a target body and a support supporting the target body; and
   a housing surrounding the target component, the housing including a first surface and a second surface allowing radiation beams to pass through;
   wherein each of a first through mounting hole and a second through mounting hole is arranged on one of the first surface and the second surface; and
   each of a first window and a second window is mounted in one of the first mounting hole and the second mounting hole.

2. The radiotherapy target device of claim 1, wherein the housing forms a sealed cavity.

3. The radiotherapy target device of claim 1, wherein the support comprises:
   a target substrate including a through hole along a beam direction of the radiation beams; and
   a target seat mounted in the through hole and used to mount the target body.

4. The radiotherapy target device of claim 3, wherein the target seat comprises:
   a mounting groove with an opening facing the first surface, wherein the mounting groove is used to mount the target body; and
   a concave part with an opening facing the second surface, wherein the concave part is used to allow the radiation beams to pass through.

5. The radiotherapy target device of claim 3, wherein the target seat includes a fixed edge;
   the through hole includes a fixed groove; and
   the fixed groove is used to mount the fixed edge to mount the target seat in the through hole.

6. The radiotherapy target device of claim 3, wherein an accommodating space is formed between an outer wall of the target seat and the through hole, the accommodating space allowing a cooling component or a cooling medium to pass through.

7. The radiotherapy target device of claim 6, wherein
   the through hole includes a first stepped hole and a second stepped hole coaxially arranged,
   the outer wall of the target seat is in contact with an inner wall of the second stepped hole, and
   the outer wall of the target seat and an inner wall of the first stepped hole are enclosed as the accommodating space.

8. The radiotherapy target device of claim 6, wherein the accommodating space is formed by a first slot in an inner wall of the through hole and/or a second slot in the outer wall of the target seat.

9. The radiotherapy target device of claim 3, further comprising a second target component, wherein
   the second target component includes a second target body,
   the target substrate further includes a second through hole along the beam direction of the radiation beams,
   the support further includes a second target seat mounted in the second through hole and used to mount the second target body, wherein
   at least part of the second target seat is sealed with the housing and the second target body is located outside of a sealed cavity formed by the housing.

10. The radiotherapy target device of claim 3, wherein the housing includes a first cover plate and a second cover plate respectively covering two opposite surfaces of the target substrate; and the first window is arranged on the first cover plate and corresponds to a position of the target body, and the second window is arranged on the second cover plate and corresponds to a position of the target body.

11. The radiotherapy target device of claim 1, wherein the support includes a flow channel, wherein
   a first end of the flow channel is connected with a cavity formed by the support; and
   a second end of the flow channel is connected with outside of the support.

12. The radiotherapy target device of claim 11, wherein the flow channel is arranged on an target substrate of the support.

13. The radiotherapy target device of claim 11, wherein the support further includes a first cover plate and/or a second cover plate, and the flow channel is arranged on the first cover plate and/or the second cover plate.

14. The radiotherapy target device of claim 11, wherein the second end of the flow channel is connected with an inert-gas source or a vacuum component.

15. The radiotherapy target device of claim 11, wherein the target component further includes an adsorption component arranged in the flow channel or an inner surface of the housing.

16. The radiotherapy target device of claim 1, wherein a cross-sectional area of the second window is larger than a cross-sectional area of the first window.

17. The radiotherapy target device of claim 1, wherein the housing includes a through hole connected with an inert-gas source or a vacuum component.

18. The radiotherapy target device of claim 1, further comprising a cooling component used to cool the target component, wherein the cooling component passes through the housing and is partially located inside the housing, and the cooling component is configured to support the support on the housing, so that at least one surface of the support is in contact with or connected to the housing.

19. The radiotherapy target device of claim 1, wherein materials of the first window and/or the second window are different from materials of other parts of the housing.

20. A radiotherapy target device, comprising:
- a target component including a target body and a support supporting the target body, and
- a housing surrounding the target component, the housing including a first surface and a second surface allowing radiation beams to pass through;
- wherein each of a first through mounting hole and a second through mounting hole is arranged on one of the first surface and the second surface; and
- each of a first window and a second window is mounted in the first mounting hole and the second mounting hole;
- the support including a flow channel, wherein
  - a first end of the flow channel is connected with a cavity formed by the support; and
  - a second end of the flow channel is connected with outside of the support.

* * * * *